United States Patent [19]

Ogawa et al.

[11] Patent Number: 4,990,603
[45] Date of Patent: Feb. 5, 1991

[54] SIALIC ACID DERIVATIVES AND PROCESS THEREFOR

[75] Inventors: Tomoya Ogawa, Musashino; Mamoru Sugimoto, Niiza; Masaaki Numata, Kawagoe; Shoji Yoshimura, Iruma; Masayoshi Ito, Kunitachi; Yoshiyasu Shitori, Tokyo, all of Japan

[73] Assignee: Mect Corporation, Tokyo, Japan

[21] Appl. No.: 68,205

[22] Filed: Jun. 30, 1987

[30] Foreign Application Priority Data

Jul. 4, 1986 [JP] Japan ................................ 61-157646
Jul. 4, 1986 [JP] Japan ................................ 61-157647
Jul. 4, 1986 [JP] Japan ................................ 61-157648

[51] Int. Cl.$^5$ ..................... C07G 3/00; C08B 37/00; C07H 19/00
[52] U.S. Cl. ................................... 536/17.4; 536/4.1; 536/17.2; 536/18.5; 536/18.7; 536/22; 536/55.2; 536/55.3; 536/115; 536/119; 536/120
[58] Field of Search ...................... 536/17.4, 17.2, 4.1, 536/18.5, 18.7, 22, 55.2, 55.3, 115, 119, 120

[56] References Cited

U.S. PATENT DOCUMENTS 4,694,076 9/1987 Ogawa et al. ...................... 536/17.2
4,751,290 6/1988 Ogawa et al. ...................... 536/17.2

FOREIGN PATENT DOCUMENTS 0264889 4/1988 European Pat. Off. ........... 536/17.4

OTHER PUBLICATIONS

Carbohydrate Research, 128 (1984) C1-C4.
Carbohydrate Research, vol. 110, 1982, pp. 11-18, Elsevier Scientific Publishing Co. Amsterdam, NL; N. Baggett et al.: "Reinvestigation of the Synthesis of 4-methylcoumarin-7-yl 5-acetamido-3, 5-dideoxy-alpha-D-glycero-D-galacto-2, nonulopyranosis-donic Acid, A Fluoro-genic Substrate . . . ".
Tetrahedron Letters, No. 78, 1979, pp. 4637-4640, Pergamon Press, Ltd. GB; U. Dabrowski et al.: "$^1$H-NMR Studies at N-acetyl-D-neuraminic Acid Ketosides for the Determination of the Anomeric Configuration II".
Carbohydrate Research, vol. 78, 1980, pp. 190-194, Elsevier Scientific Publishing Co. Amsterdam, NL; V. Eschenfelder et al.: "A New Approach to the Synthesis of 5-N-acetyl-D-neuraminic and Acid Alpha-Ketosides".
Chemical Abstracts, vol. 87, No. 13, Sep. 26, 1977, pp. 651, 652 Abstract No. 102561x Columbus, Ohio, U.S.; H. J. Jennings et al.: "Isolation of 9-O-(alpha-D-N-acetylneuraminyl)-beta-D-B-acetylneuraminic Acid by Partial Acid Hydrolysis, and Its Characterization by Carbon-13 NMR" & Carbohydr. Res. . . . .

Primary Examiner—Ronald W. Griffin
Assistant Examiner—Everett White
Attorney, Agent, or Firm—Oblon, Spivak, McClelland, Maier & Neustadt

[57] ABSTRACT

The present invention relates to sialic acid derivatives.

According to the present invention, there is provided sialic acid derivatives having the general formula (I):

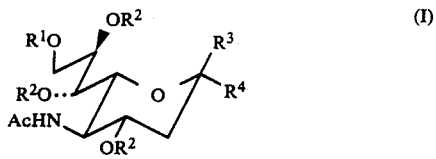

(I)

wherein, $R^1$ represents hydrogen, an acetyl group, a trityl group,

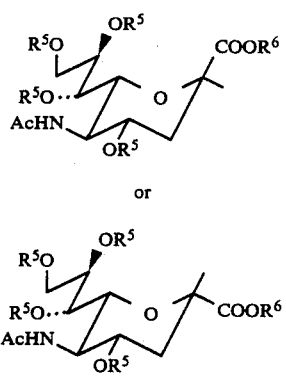

or ($R^5$ represents hydrogen or an acetyl group and $R^6$ represents hydrogen, sodium or a methyl group).

$R^2$ represents hydrogen or an acetyl group, one of $R^3$ and $R^4$ represents

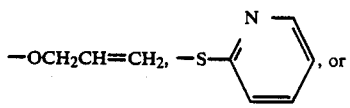

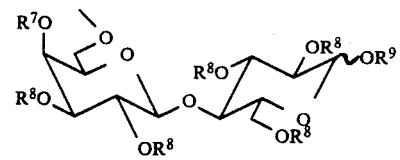

($R^7$ represents a hydrogen atom or an acetyl group, $R^8$ represents a hydrogen atom, an acetyl group or a benzyl group, $R^9$ represents a hydrogen atom, an acetyl group, a benzyl group or

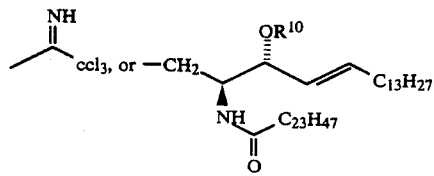

wherein $R^{10}$ represents a hydrogen atom or a benzoyl group), while the other represents —COOR$^{11}$ wherein $R^{11}$ represents hydrogen, sodium, or a methyl group.

11 Claims, No Drawings

SIALIC ACID DERIVATIVES AND PROCESS THEREFOR

BACKGROUND OF THE INVENTION

The present invention relates to new sialic acid derivatives, in particular, gangliosides or intermediates for producing gangliosides.

In general, glycolipids of mammal cells are the substances which are formed by glycoside linkage between various combinations of various sugars such as glucose, galactose, N-acetylglucosamine, N-acetylgalactosamine, fucose and sialic acid, and a lipid structure called ceramide which in turn is formed through an amide linkage between fatty acid and long-chain aminoalcohol known to as sphingosine. And, these glycolipids belong to a so-called sphingoglycolipid. Among these glycolipids, those which have sialic acid are specifically called gangliosides.

Generally, such compounds locally exist in the outer molecular layer of the bi-layer structure of cell membrane. The current study has proved that these compounds play important roles in cells, such as identification of cells, reception and response to information, receptor function, differentiation, and proliferation, malignant alteration and behavior of cells, and so forth.

It is, however, extremely difficult to isolate oligosaccharides containing sialic acid from a living body. Therefore, fine synthesis of those oligosaccharides is indispensable for clarification of correlation between the accurate biological information and molecular structures of the saccharides.

SUMMARY OF THE INVENTION

Accordingly, an object of the present invention is to provide sialic acid derivatives useful as an intermediate for the synthesis of gangliosides, as well as a method of producing such substances.

The present invention is concerned with sialic acid derivatives having the following general formula (I):

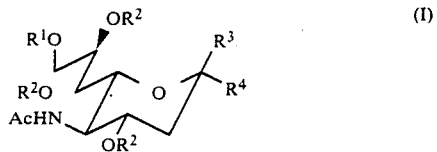

(I)

wherein, $R^1$ represents hydrogen, an acetyl group, a trityl group,

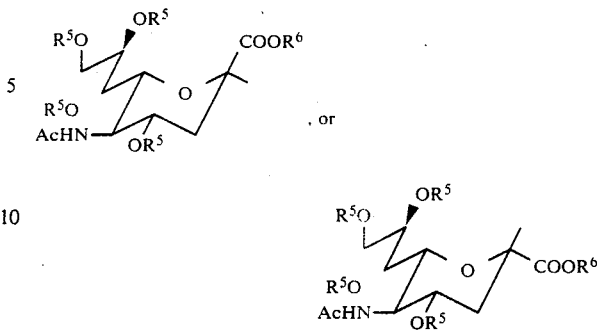

($R^5$ represents hydrogen or an acetyl group and $R^6$ represents hydrogen, sodium or a methyl group)
$R^2$ represents hydrogen or an acetyl group,
one of $R^3$ and $R^4$ represents chlorine, —OAc, —OH,

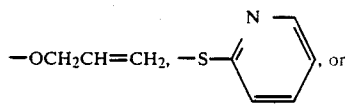

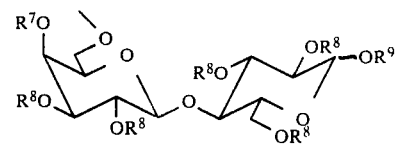

($R^7$ represents a hydrogen atom or an acetyl group, $R^8$ represents a hydrogen atom, an acetyl group or a benzyl group, $R^9$ represents a hydrogen atom, an acetyl group, a benzyl group

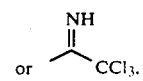

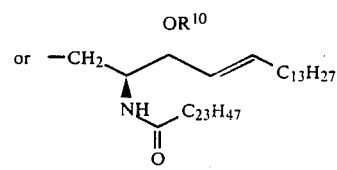

wherein $R^{10}$ represents a hydrogen atom or a benzoyl group), while the other represents —COOR$^{11}$ wherein $R^{11}$ represents hydrogen, sodium, or a methyl group.

DETAILED DESCRIPTION OF THE INVENTION

The present invention will be explained in detail below by referring to the following process diagrams.

First, explanation will be made by referring to Process diagram 1.

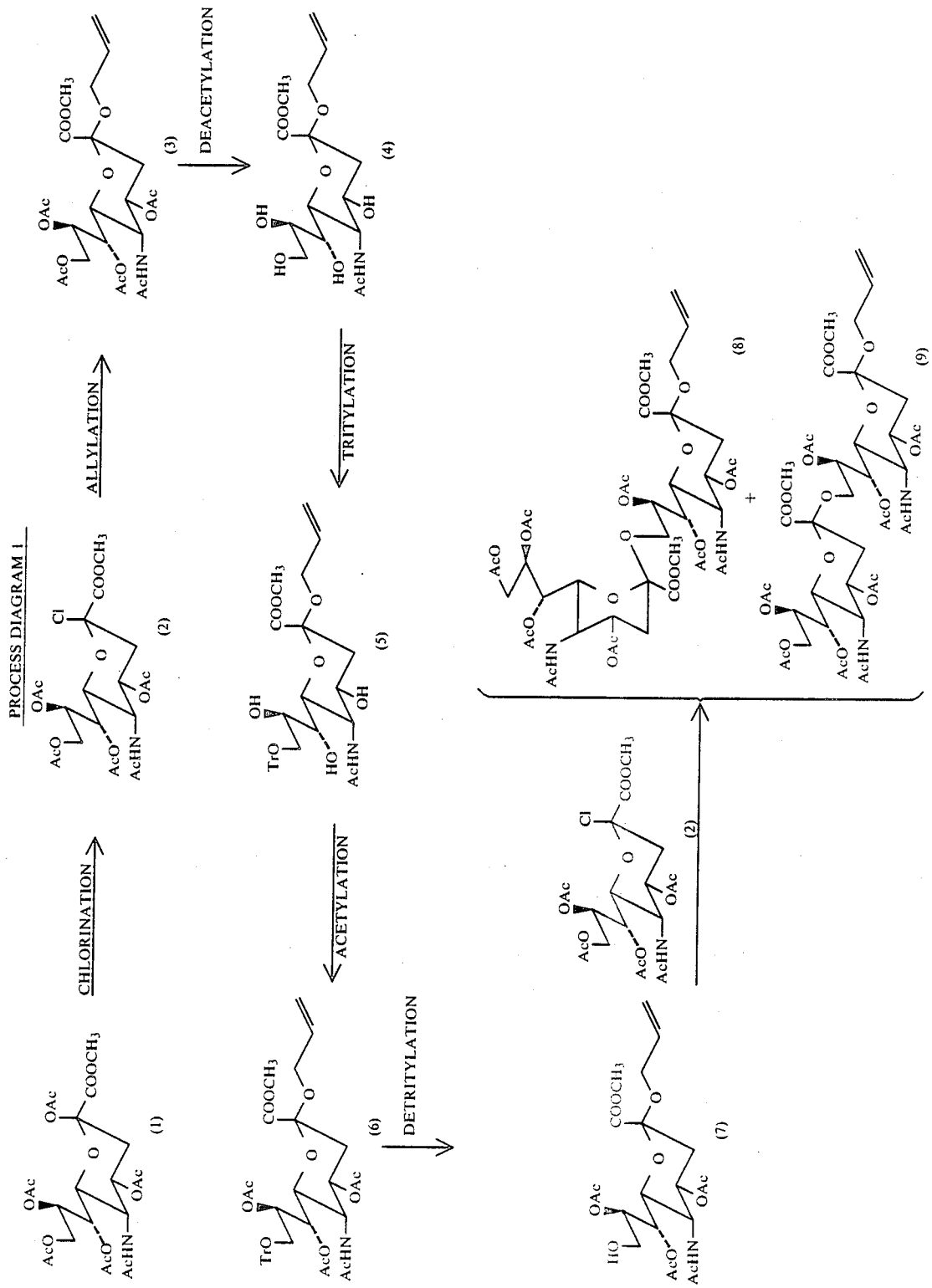

In the first step, the compound (1) is dissolved in acetylchloride and the solution is saturated with hydrogen chloride gas while being cooled by ice, followed by stirring at 3 to 24 hours at room temperature, thus obtaining the compound (2). Then, the compound (2) is dissolved in allyl alcohol and silver salicylate is added to the solution. The solution is then stirred for 5 to 24 hours at room temperature, to obtain the compound (3).

The compound (3) is then dissolved in methanol and sodium methoxide is added to the solution. The resultant solution is then stirred for 2 to 24 hours at room temperature, to obtain the compound (4).

Then, the compound (4) is dissolved in pyridine, to which tritylchloride is added. Then, the resultant solution is stirred for 3 to 24 hours at room temperature, to obtain the compound (5).

The compound (5) is dissolved in pyridine and acetic anhydride is added to the solution, followed by stirring the solution for 2 to 24 hours at room temperature, to obtain the compound (6).

Then, 90% aqueous solution of acetic acid is added to the compound (6) and the thus obtained mixture is stirred for 2 to 24 hours at a temperature ranging between room temperature and 80° C., to obtain the compound (7).

The compound (7) and the compound (2) are dissolved in anhydrous tetrahydrofuran, and the thus formed mixture is added to activated molecular sieves 4A. Then, silver triflate (AgOTf) dissolved in anhydrous tetrahydrofuran is added to the molecular sieve containing the compounds (7) and (2), while the molecular sieves are stirred at a temperature between $-30°$ and 30° C. Then, after lapse of 0.5 to 6 hours, the compound (2) dissolved in anhydrous tetrahydrofuran is added thereto, and stirring is effected for 2 to 24 hours at a temperature between $-30°$ and 30° C., whereby the compounds (8) and (9) are obtained.

Secondly, another process for producing the present compounds will be explained by referring to Process diagram 2.

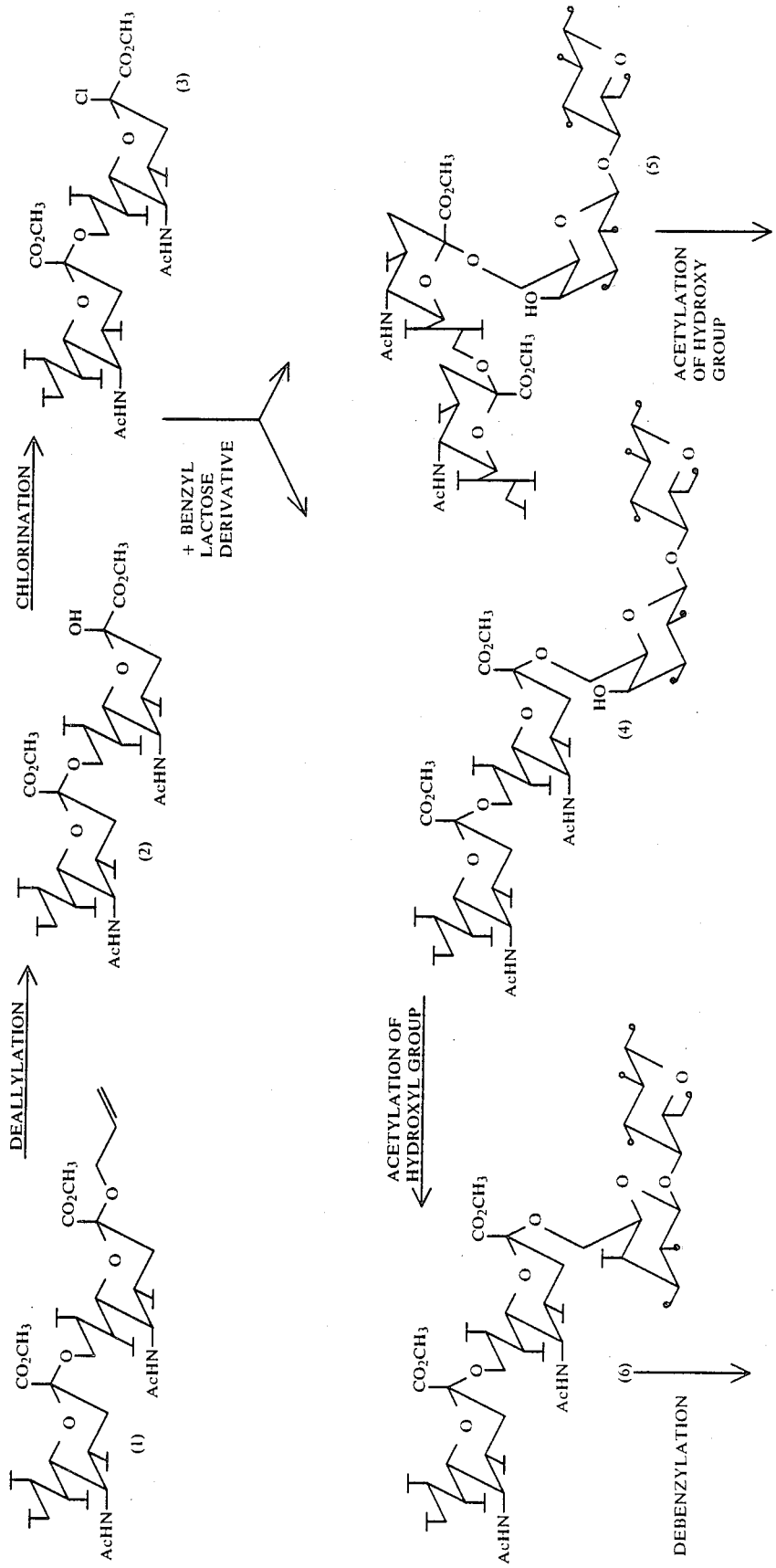
PROCESS DIAGRAM 2

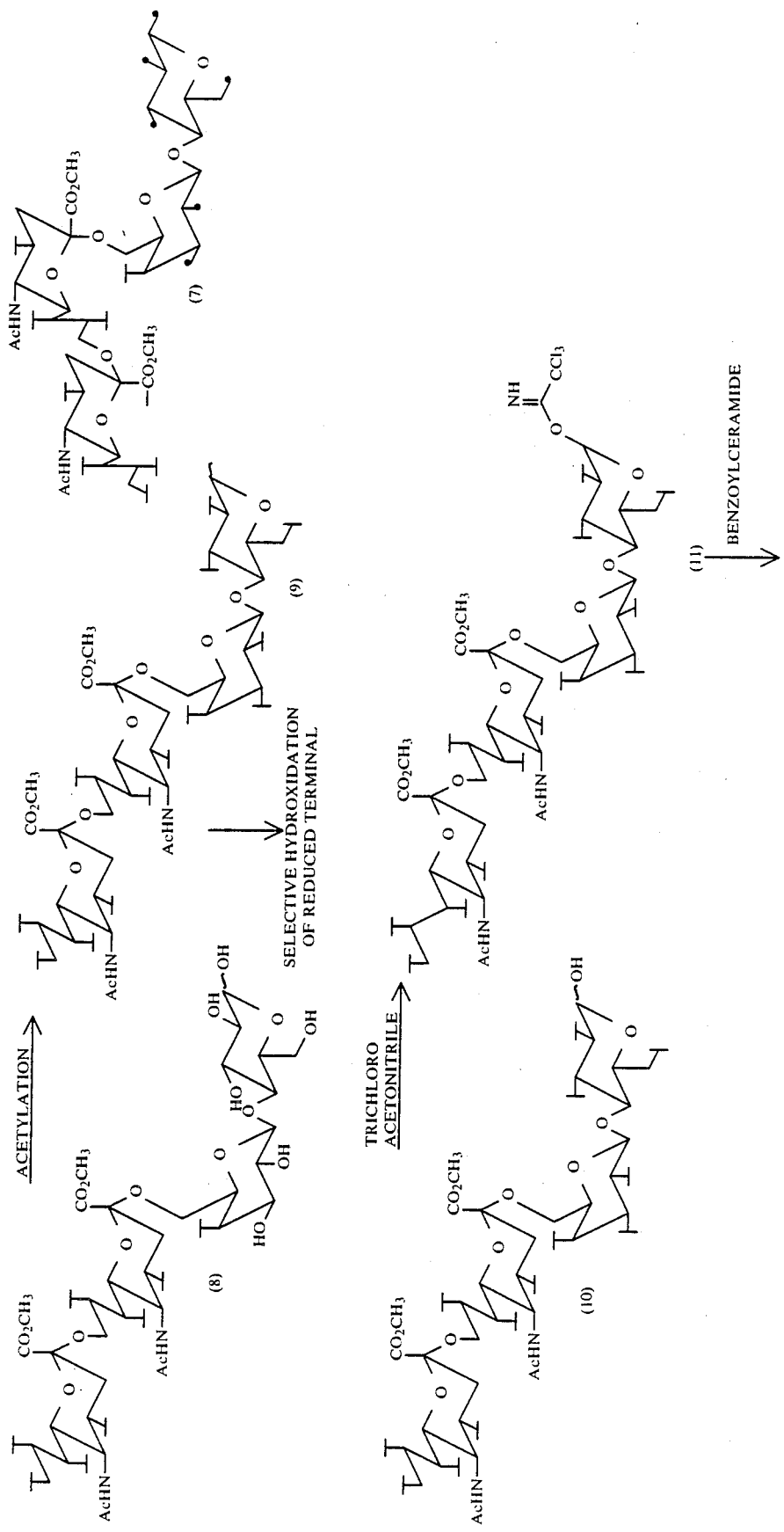

-continued
PROCESS DIAGRAM 2
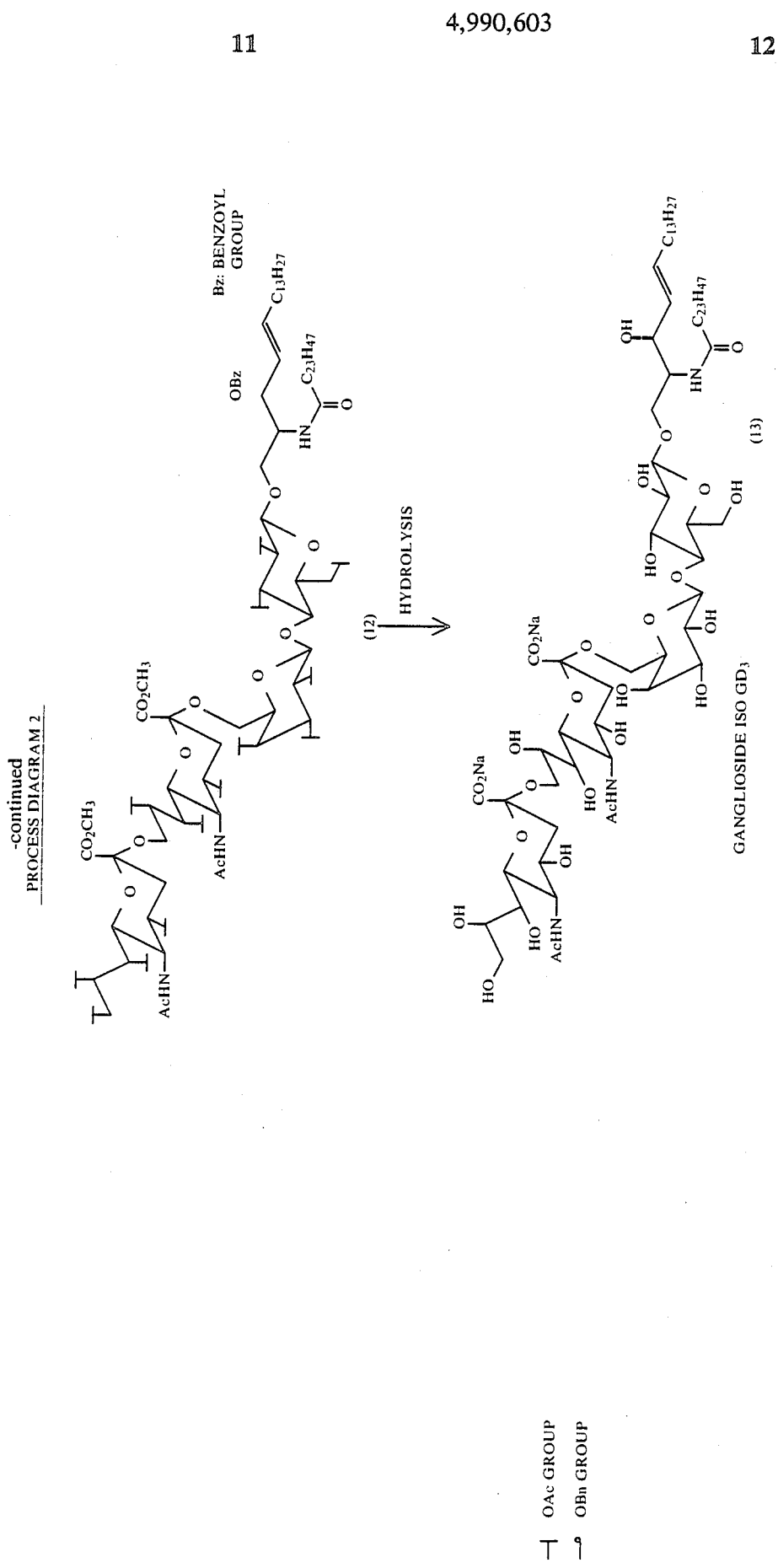

The compound (1) is subjected to deallylation, to obtain the compound (2), which in turn is then chlorinated to convert the compound (2) into the compound (3). Then, the compound (3) is reacted with benzyl lactose to obtain the compounds (4) and (5). Then, the hydroxy groups of the compounds (4) and (5) are acetylated, to obtain the compounds (6) and (7), respectively. The compound (6) is then changed into the compound (8) through debenzylation, and the compound (8) is further changed into the compound (9) through acetylation. The compound (9) is then changed into the compound (10) through hydroxylation, and trichloroacetonitrile is made to react with the compound (10), whereby the compound (11) is obtained. Then, benzoylceramide is made to react with the compound (11), to obtain the compound (12). The compound (12) is subjected to hydrolysis whereby the compound (13), ganglioside iso $GD_3$, is obtained.

In this case, the compound (1) corresponds to the compound (9) shown in the Process diagram 1, and the process therefor is shown in the diagram.

Specifically speaking, the compound (1) is dissolved in a mixture solvent of ethanol:water:acetic acid=20:5:1. Then, 10% Pd-C is added to the resultant solution, which is then stirred for 5 hours to 4 days at room temperature. The reaction solution is filtrated by Celite and iodine is added to the filtrated solution, followed by stirring for 15 to 60 minutes at room temperature. The reaction solution is then diluted with water, and chloroform is added to the diluted solution. After washing with water, the solution is further washed with sodium and then with saturated brine. The solution is then dehydrated with anhydrous magnesium sulfate and then the solution medium is distilled off, to obtain the compound (2).

The compound (2) is dissolved in tetrahydrofuran, to which toluene and Vilsmeier's reagent [J.C.S., Perkin I, 754–757 (1976)] are added. The resultant mixture is stirred for 2 hours to one day at room temperature, whereby the compound (3) is obtained from the reaction solution.

A tetrahydrofuran solution of benzyl lactose and a tetrahydrofuran solution of the compound (3) are added to molecular sieves, and the mixture is stirred for 15 to 60 minutes at room temperature. Then, while the mixture is cooled by ice-methanol, a tetrahydrofuran solution of silver triflate and a tetrahydrofuran solution of tin chloride are added to the mixture. After lapse of 30 minutes to 2 hours, a tetrahydrofuran solution of the compound (3) is added and the mixture is stirred for 3 hours to 2 days, thus obtaining the compounds (4) and (5).

The compounds (4) and (5) are dissolved in pyridine and acetic anhydride, respectively, and dimethylaminopyridine is added to the respective solutions. These solutions are stirred at room temperature for about 2 to 24 hours, to obtain the compounds (6) and (7). Subsequently, the compound (6) is dissolved in methanol, and is reduced with 10% Pd-C at room temperature for 2 hours to 2 days, whereby the compound (8) is obtained.

The compound (8) is dissolved in pyridine acetic anhydride and dimethylaminopyridine is added to the solution, followed by stirring for about 3 to 24 hours, whereby the compound (9) is obtained.

The compound (9) is dissolved in N,N-dimethylformamide and hydrazinium acetate is added to the solution. The mixture is then stirred at 5 to 40 minutes at a temperature ranging between room temperature and 80° C., whereby the compound (10) is obtained.

The compound (10) is dissolved in methylene chloride and, while the solution is cooled by ice, trichloroacetonitrile and 1,8-diazabicyclo[5,4,0]-7-undecen are added to the solution. The mixture is then stirred for 1 to 2 hours, whereby the compound (11) is obtained.

The compound (11) and a chloroform solution of benzoylceramide are added to molecular sieves, and, after stirring for 10 to 30 minutes, boron triflouride-ether complex is added to the mixture while the latter is cooled by ice, followed by stirring for about 3 hours to one day, whereby the compound (12) is obtained.

The compound (12) is dissolved in methanol and tetrahydrofuran and sodium methoxide is added to the solution. The solution is then stirred for 2 hours to one day at room temperature, and the reaction solution is subjected to distillation under reduced pressure Subsequently, methanol, tetrahydrofuran and water are added to the residue, and stirring is conducted at room temperature for 2 hours to one day. The reaction solution is then neutralized with IRC-50, to obtain the compound (13).

Further, another process for producing the present compounds will be explained by referring to Process diagram 3.

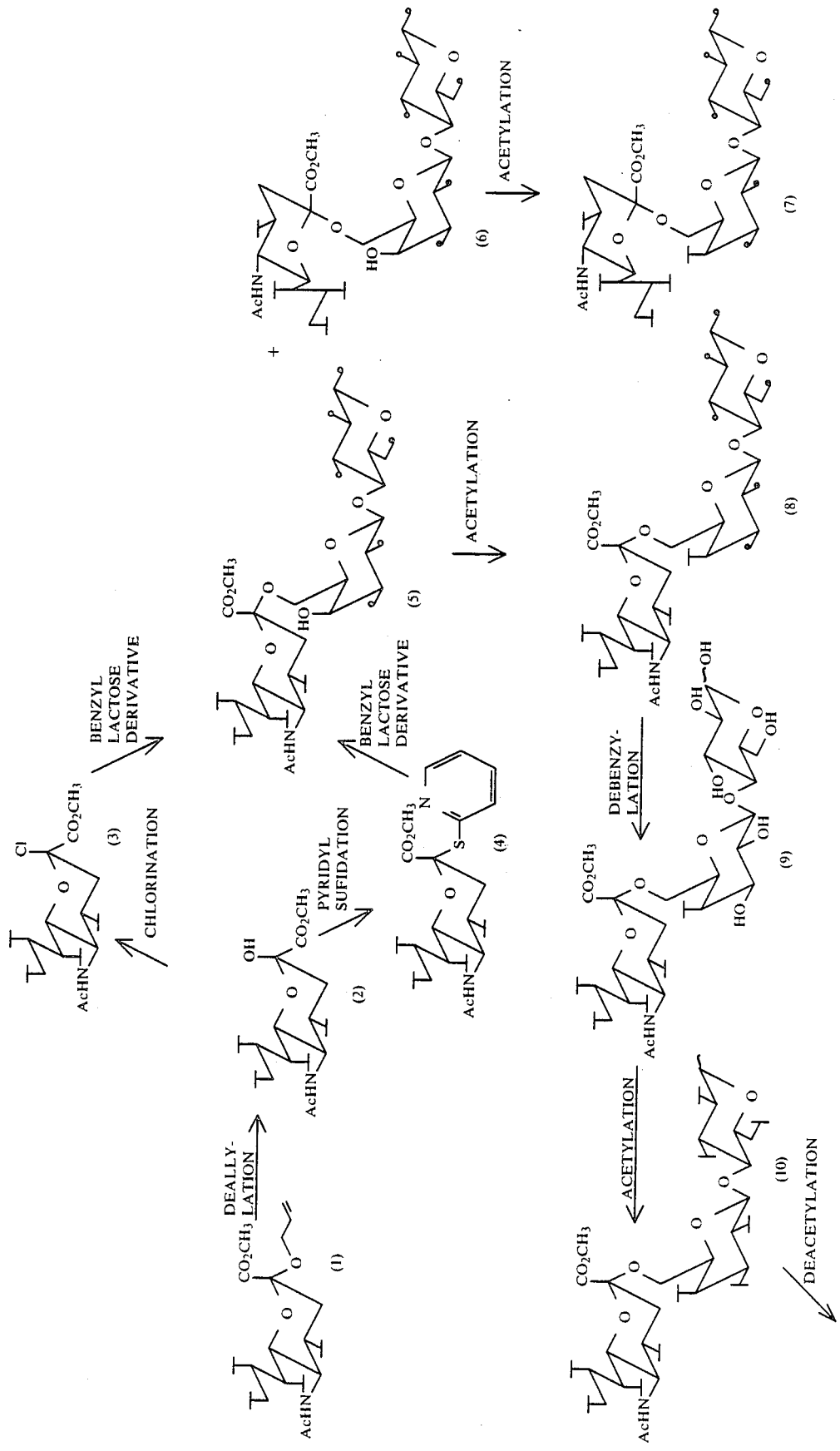

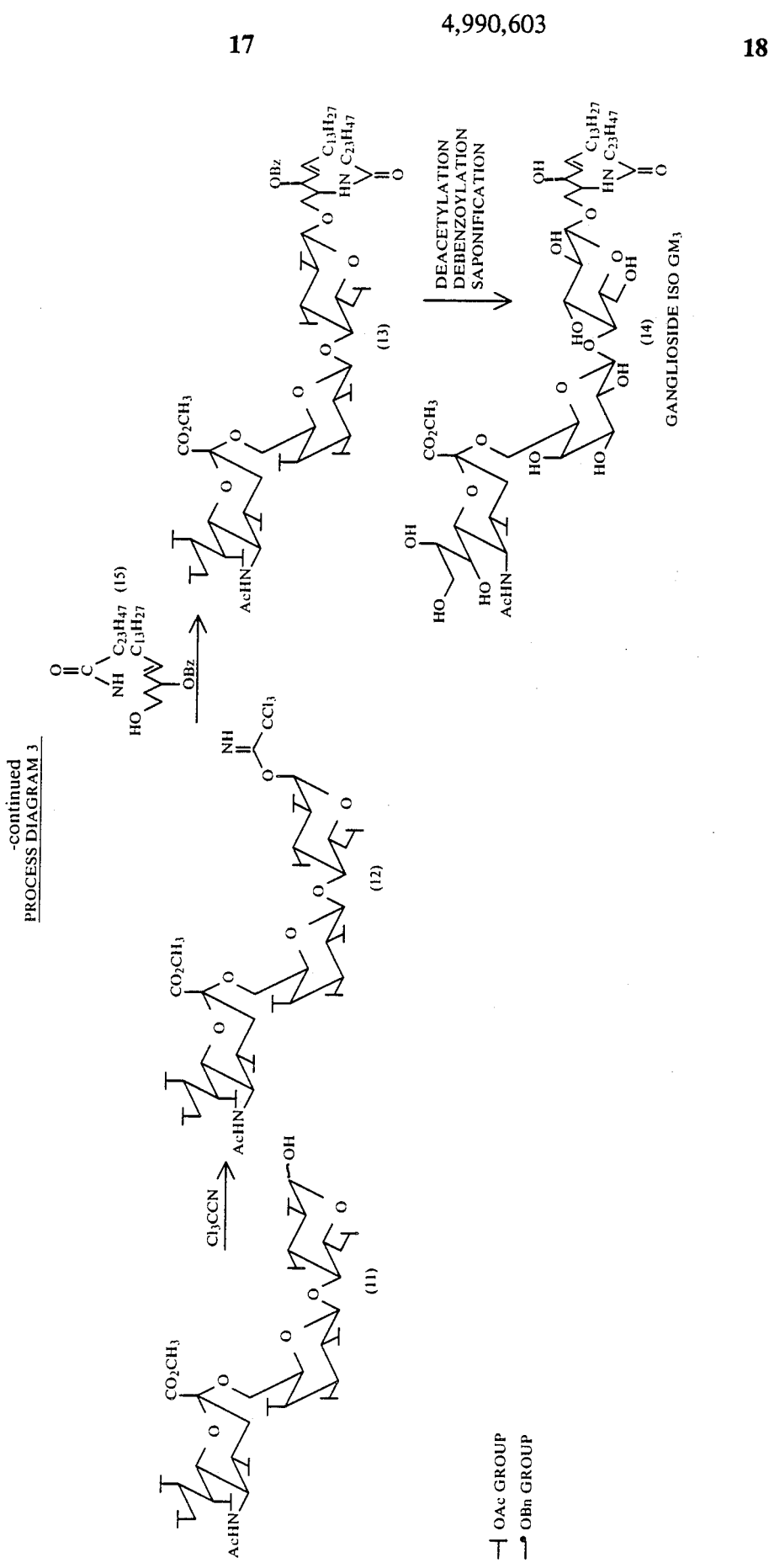

The compound (1) is subjected to deallylation to obtain the compound (2), which in turn is then chlorinated to produce the compound (3). Meanwhile, the compound (4) is obtained through pyridylsulfidization of the compound (2). The compounds (5) and (6) are formed by causing benzyl lactose to react with the compounds (3) and (4), respectively. Then, the compounds (5) and (6) are acetylated to produce the compounds (8) and (7). The compound (8) is debenzylated to produce the compound (9), which in turn is acetylated to produce the compound (10). The compound (10) is deacetylated to produce the compound (10). The compound (11) is then made to react with $Cl_3CCN$ so as to form the compound (12). The compound (12) is then made to react with the compound having the following formula (15), to produce the compound (13).

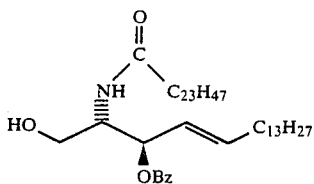
(15)

(Bz represents a benzoyl group)

The compound (13) is then subjected to deacetylation, debenzoylation and saponification, whereby ganglioside iso $GM_3$ expressed by the general formula (14) is obtained.

This production method will be explained more detail hereinunder.

10% Pd-C is added to the compound (1) in EtOH-$H_2O$-AcOH (20:5:1) and the mixture is stirred for 1 hour to 4 days at a temperature between room temperature and 100° C., followed by filtration by Celite. The filtrated liquid is then condensed under reduced pressure. To the reaction liquid, 80% THF of iodine is added. The mixture is then stirred for 15 to 60 minutes at room temperature and the reaction solution is diluted with water. Then, the diluted solution is washed with water after addition of chloroform. The solution is then washed by aqueous $NaHSO_3$ solution and then by saturated brine. The washed solution is then dehydrated with $MgSO_4$ and the solution medium is distilled off to produce the deallylated compound (2).

Then, Vilsmeier's reagent (J.C.S. Perkin 1, 754–757 (1976)) is added and the mixture is stirred at room temperature for 2 to 24 hours to obtain the chlorinated compound (3).

THF solution of benzyl lactose and THF solution of the compound (3) are added to molecular sieves. After stirring at room temperature for 15 to 60 minutes, THF solution of silver triflate (AgOTf) and THF solution of $SnCl_2$ are added to the mixture while the mixture is being cooled by ice-MeOH. The mixture is then stirred for 2 to 48 hours and filtrated by Celite. The filtrated liquid is then washed by aqueous solution of saturated sodium bicarbonate, water and saturated brine. The washed mixture is then dried by anhydrous $MgSO_4$ and the mixture medium is distilled off to form the compounds (5) and (6).

2,2'-Dipyridylsulfide and tributylphosphine are added to the compound (2) in dichloromethane. The resultant mixture is stirred at room temperature for 2 to 48 hours to obtain the compound (4). Subsequently, a dichloroethane solution of benzyl lactose and a dichloroethane solution of AgOTf are added to molecular sieves. While the mixture is cooled by ice-MeOH, $SnCl_2$ and a dichloroethane solution of the compound (4) are added thereto. The mixture is then stirred for 1 to 24 hours at 30° to 60° C. and is filtrated by Celite. The flitrated liquid is washed by an aqueous solution of saturated sodium bicarbonate and saturated brine, and the washed solution is distilled off after drying by anhydrous $MgSO_4$, whereby the compounds (5) and (6) are obtained. Then, pyridine and acetic anhydride are added to the compound (6) so as to dissolve the latter. Then, dimethyl aminopyridine is added to the dissolved compound (6) and the mixture is stirred for 1 to 24 hours at room temperature, to obtain the acetylated compound (7). A similar process is carried out on the compound (5), to obtain the compound (8).

10% Pd-C is added to the compound (8) in methanol. The mixture is then catalytically reduced at room temperature for about 2 to 24 hours so as to obtain the compound (9).

The compound (9) is then dissolved by addition of pyridine and acetic anhydride, and dimethyl aminopyridine is added to the dissolved compound (9). The mixture is then stirred at room temperature, obtain the acetylated compound (10).

The compound (10) is then dissolved in DMF, to which $H_2N.NH_2AcOH$ is added. After the resultant solution is stirred for 5 to 60 minutes at a temperature between room temperature and 80° C., EtOAc is added to the solution, which is then washed with saturated brine and dried by anhydrous $MgSO_4$, followed by distilling-off, to obtain the compound (11).

The compound (11) is dissolved in methylene chloride, to which trichloroacetonitrile and DBU (1,8-diazobicyclo [5,4,0] undeca-7-en) are added. The resultant mixture is stirred for 1 to 4 hours, to obtain the compound (12).

Chloroform solution of the compound (12) and the compound (15) having the following formula (15) are added to molecular sieves.

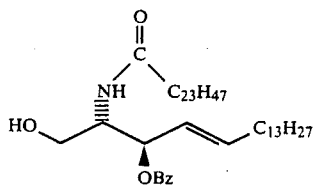
(15)

(Bz represents a benzoyl group)

Then, $BF_3.Et_2O$ is added to the mixture while the latter is cooled by ice-MeOH and the thus formed mixture is stirred for 1 to 24 hours. After filtration by Celite, the mixture is distilled off under reduced pressure, to obtain the compound (13).

The compound (13) is dissolved in a mixture solvent of MeOH:THF of 1:1, which is then stirred at room temperature for 2 to 24 hours. After distilling-off of the medium of the reaction solution, MeOH, THF and $H_2O$ are added to the residual material, which is stirred at room temperature for about 2 to 24 hours. The reaction liquid is then neutralized by IRC-50, followed by filtration, and the filtrated liquid is distilled off under reduced pressure, whereby the ganglioside iso$GM_3$ (14) is obtained as the final product.

UTILITY OF THE INVENTION

Novel compounds of the present invention described above are useful as tumor markers and cell differentiation markers having differentiation inducibility, or as synthesis intermediates of such markers.

Examples of the present invention will be described hereinunder. In the following description of Examples, the numbers of compounds are the same as those appearing in respective process diagram.

EXAMPLE

A. Examples concerning the process shown in Process diagram 1

REFERENCE EXAMPLE 1

The compound (3) was prepared as follows, in accordance with the teaching of Carbohydr. Res. 78: (1980), 190–194.

10 g (18.3 mmol) of the compound (1) was dissolved in 50 g of acetylchloride and the solution was saturated with hydrogen chloride gas while being cooled by ice, followed by stirring for 15 hours at room temperature. After distilling off the medium of the reaction solution, ether was added to the residual material and then distillation was repeated. In consequence, caramel-like compound (2) was obtained in an amount of 9.02 g (94%).

Then, 8.42 g (11.5 mmol) of the compound (2) was dissolved in 70 ml of allyl alcohol, and 5.36 g (21.9 mmol) of silver salicylate was added to the solution. The solution was then stirred for 15 hours at room temperature. The resultant reaction solution was filtrated by suction and then condensed under reduced pressure. To the condensed solution, ethyl acetate was added and the ethyl acetate layer was washed by water, 5% sodium thiosulfate, saturated sodium bicarbonate and saturated brine. The washed solution was then dried by anhydrous magnesium sulfate, followed by distillation-off of the solution medium under reduced pressure. The reaction product was then refined by silica gel column [Wakogel (produced by Wako Junyaku Kogyo Kabushiki Kaisha) C-300, 300 g, chloroform:ethanol=4:1], to obtain the compound (3) in an amount of 8.05 g (91%).

Rf=0.57 (chloroform:ethanol=4:1)
melting point 155° to 175° C.

EXAMPLE 1

29 g (54.6 mmol) of the compound (3) was dissolved in 200 ml of methanol and 20 ml of sodium methoxide was added to the solution, followed by stirring for 2 hours at room temperature. Then, Amberlist 15, ion exchange resin (produced by Roam and Hearth Co., U.S.A.) was added to the reaction solution so as to neutralize the solution, followed by filtration and distillation of the solution medium under reduced pressure, whereby the compound (4) was obtained in an amount of 18.9 g (85%).

Rf=0.05 (chloroform:ethanol=4:1).
Rf=0.25 (chloroform:methanol=5:1).
$[\alpha]^{23}$ −3.0 (c=1.0 methanol).
Element analysis $C_{15}H_{25}NO_9 \cdot \frac{1}{2} H_2O$. Calculated value: C, 48.40; H, 7.04; N, 3.76. Measured value: C, 48.51; H, 6.76; N, 3.7.

EXAMPLE 2

8.5 g (23 mmol) of the compound (4) was dissolved in 100 ml of pyridine and 9 g (31.5 mmol) of tritylchloride was added to the solution, followed by stirring for 6 hours at 50° C. Then, triethylamine was added to the reaction solution and the solution medium was distilled off under reduced pressure. To the resultant material, chloroform was added, and the chloroform layer was washed by water. Then, the washed solution was dried with anhydrous magnesium sulfate, followed by distilling-off of the solution medium. The reaction product was then refined by a silica gel column (Wakogel C-300, 300 g, toluene ethyl acetate=1 5), whereby the compound (5) was obtained in an amount of 9.6 g (72.8%).

Rf=0.74 (chloroform:methanol=3:2).
Element analysis $C_{19}H_{33}O_9N$. Calculated value: C, 67.42; H, 6.49; N, 2.3. Measured value: C, 67.51; H, 6.39; N, 2.23. $[\alpha]^{21}$ −5.2° (chloroform c=1.01).

EXAMPLE 3

8.0 g (13.2 mmol) of the compound (5) was dissolved in 50 ml of pyridine, to which 50 ml of acetic anhydride was added. The solution was then stirred for 15 hours at room temperature. The reaction solution was then subjected to azeotropic distillation with toluene for 5 times, followed by distilling-off of the solution medium under reduced pressure The residue was recrystallized, whereby the compound (6) was obtained in an amount of 9.47 g (97.5%).

Melting point 216° to 218° C.
Rf: 0.65 (toluene:ethyl acetate=1:5).
$[\alpha]^{22}$ +0.2 (chloroform c=1.0).
Element analysis $C_{40}H_{45}NO_{12}$. Calculated value: C, 65.65; H, 6.20; N, 1.91. Measured value: C, 65.70; H, 6.21; N, 1.90.

EXAMPLE 4

120 ml of a 90% aqueous solution of acetic acid was added to 9.46 g (12.9 mmol) of the compound (6), and stirring was effected for 5 hours at 55° C. The reaction solution was then condensed under reduced pressure and ethyl acetate was added to the condensed solution. The ethyl acetate layer was then washed by saturated sodium bicarbonate and water, and dehydration was conducted with anhydrous magnesium sulfate, followed by distilling-off of the solution medium under reduced pressure. The reaction product was then refined by a silica gel column (Wakogel C-300, 600 g, ethyl acetate:methanol=10:0.2), whereby the compound (7) was obtained in an amount of 3.29 g (52%).

Rf: 0.29 (ethylacetate:methanol=10:0.3).
$[\alpha]^{22}$ −29.4° (chloroform c=0.93).
Element analysis $C_{21}H_{31}NO_{12}$. Calculated value: C, 51.53; H, 6.38; N, 2.68. Measured value: C, 50.92; H, 6.34; N, 2.79.

EXAMPLE 5

To 2 ml of anhydrous tetrahydrofuran, there were added 300 mg (0.6 mmol) of the compound (7), 398 mg (0.78 mmol) of the compound (2), and 1.5 g of activated molecular sieves 4A. While the mixture was stirred at −10° C., 2 ml of anhydrous tetrahydrofuran containing 462 mg (1.8 mmol) of silver triflate was added to the mixture. After lapse of 2 hours, 2 ml of anhydrous tetrahydrofuran containing 214 mg (0.42 mmol) of the compound (2), and the mixture was stirred for 3 hours at −10° C. The reaction solution was then filtrated through Celite and ethyl acetate was added to the filtrated solution. The ethyl acetate layer was washed by saturated sodium bicarbonate and then by water. Subsequently, dehydration was conducted with anhydrous magnesium sulfate, followed by distillation-off of the solution medium under reduced pressure. The reaction product was then refined by a silica gel column (Wakogel C-300, 100 g, 5% methanol-ethylacetate, then C-300, 50 g, carbon tetrachloride:acetone 1:1), whereby compounds (8) and (9) were obtained.

Property of Compound (8)

$[\alpha]^D$ −8.2 (chloroform c=1.02).

Element analysis $C_{41}H_{58}O_{24}N_2$. Calculated value: C, 51.14; H, 6.07; N, 2.91. Measured value: C, 51.42; H, 6.91; N, 2.93.

NMR 400 MHz, $CDCl_3$, ppm, TMS 1.902, 2.010, 2.017, 2.036, 2.095, 2.157, 2.184, ($-COCH_3 \times 9$), 2.427, 1H, dd, J=4.88, 12.94, H-2beq, 2.607, 1H, dd, J=4.64, 12.70, H-2aeq, 3.785, 3H, s, $OCH_3$, 3.794, 3H, s, $OCH_3$, 4.89, 1H, m, H-4a, 5.15, 1H, m, H-4b.

Property of Compound (9)

$[\alpha]_{23}^D$ −17.8 (chloroform c=0.98).

Element analysis $C_{41}H_{58}O_{24}N_2$. Calculated value: C, 51.14; H, 6.07; N, 2.91. Measured value: C, 50.68; H, 6.04; N, 2.8.

NMR 400 MHz, $CDCl_3$, ppm, TMS 1.875, 1.903, 2.021, 2.028, 2.058, 2.111, 2.132, 2.144, 2.167, s, $COCH_3 \times 9$, 1.964, 2H, t, J=7.81, H-3aax, H-3bax, 2.570, 1H, dd, J=4.64, 12.94, H-3eq, 2.619, 1H, dd, J=4.15, 12.45, H-3eq, 3.786, 3H, s, $OCH_3$, 3.790, 3H, s, $OCH_3$ 4.862, 2H, m, H-4a, H-4b.

B. Examples concerning the process shown in Process diagram 2

EXAMPLE 1

500 mg (0.52 mmol) of the compound (1) was dissolved in 20 ml of a mixed solvent of ethanol, water and acetic acid at a ratio of ethanol:water:acetic acid=20:5:1. Then, 250 mg of 10% Pd-C was added to the mixture, which was stirred for 2 days at 60° C. The reaction solution was filtrated by Celite and the solution medium was distilled off under reduced pressure. Then, 40 ml of 80% tetrahydrofuran (20% water) was added to the residue, and 429 mg (1.8 mmol) of iodine was added thereto, and stirred for 30 minutes at room temperature. The reaction solution was then diluted with water and chloroform was added to the diluted solution. The mixture was then washed with water, followed by washing with an aqueous solution of sodium hydrogen sulfate and then by washing with saturated brine. The washed solution was then dried with anhydrous magnesium sulfate and then the solution medium was distilled. The residue was refined by a silica gel column (Wakogel by Wako Junyaku Kabushiki Kaisha: C-300, 50 g, chloroform:methanol=10:0.5), whereby the compound (2) was obtained in an amount of 400 mg (83.5%).

Rf=0.23 (chloroform:methanol=10:0.5).

Element analysis $C_{38}H_{54}N_2O_{24}+2H_2O$. Calculated value: C, 47.60; H, 6.09; N, 2.91. Measured value: C, 47.82; H, 5.69; N, 2.89.

EXAMPLE 2

380 mg of the compound (2) was dissolved in 10 ml of tetrahydrofuran, to which 4 ml of toluene and 960 mg (7.5 mmol) of Vilsmeier's reagent were added. The mixture was then stirred for 15 hours at room temperature. The reaction solution was then refined by a silica gel column (Wakogel C-300, 20 g, chloroform:methanol=10:0.5), whereby the compound (3) was obtained in an amount of 361 mg (94.5%).

Rf=0.25 (chloroform:methanol=10:0.5).

EXAMPLE 3

4 ml of tetrahydrofuran solution containing 845 mg (0.96 mmol) of 4,6-free-benzyl lactose and 1 ml of tetrahydrofuran solution containing 180 mg (0.19 mmol) of the compound (3) were added to 1.5 g of molecular sieves. The mixture was then stirred for 30 minutes at room temperature.

Then, while the mixture was cooled with ice-methanol, 1 ml of tetrahydrofuran solution containing 800 mg (3.1 mmol) of silver triflate and 1 ml of tetrahydrofuran solution containing 200 mg (1.05 mmol) of tin chloride were added to the mixture. After lapse of 2 hours, 1 ml of tetrahydrofuran solution containing 181 mg (0.19 mmol) of the compound (3) was added to the resultant solution, followed by stirring for 15 hours. The reaction solution was then filtrated with Celite and the filtrated solution was washed with a saturated aqueous solution of sodium bicarbonate and then with saturated brine. The washed solution was then dried by anhydrous magnesium sulfate, followed by distilling-off of the solution medium. The residue was then refined by a silica gel column (Wakogel C-300, 100 g, chloroform:methanol=10:0.5), whereby the compound (4) and the compound (5) were obtained in amounts of 74.1 mg (10.4%) and 11.7 mg (1.6%), respectively.

Property of Compound (4)

Rf=0.26 (chloroform:methanol=10:0.5).

$[\beta]_D^{20}$ −11.74 (c=0.855, chloroform).

Element analysis $C_{92}H_{110}O_{34}N_2+2H_2O$. Calculated value: C, 61.75; H, 6.20; N, 1.57. Measured value: C, 62.11; H, 6.12; N, 1.55.

Property of Compound (5)

Rf=0.29 (chloroform:methanol=10:0.5).

$[\beta]_D^{20}$ −9.67 (c=0.335, chloroform).

EXAMPLE 4

13 mg (0.007 mmol) of the compound (5) was dissolved in a mixture of 3 ml of pyridine with 3 ml of acetic anhydride. Then, 8 mg of dimethyl aminopyridine was added to the solution, which was stirred for 15 hours at room temperature. The medium of the reaction solution was then distilled off under reduced pressure and the residue was refined by a silica gel column (Wakogel C-300, 10 g, chloroform:methanol=10:0.5), whereby the compound (7) was obtained in an amount of 11.2 mg (84%).

Rf=0.39 (chloroform:methanol=10:0.5.

Element analysis $C_{94}H_{112}O_{35}N_2+H_2O$. Calculated value: C, 60.51; H, 6.26; N, 1.50. Measured value: C, 60.31; H, 5.79; N, 1.83.

EXAMPLE 5

93.8 mg (0.052 mmol) of the compound (4) was dissolved in a mixture of 4 ml of pyridine with 4 ml of acetic anhydride. Then, 16 mg of dimethyl aminopyridine was added to the solution, which was stirred for 15 hours at room temperature. The medium of the reaction solution was then distilled off under reduced pressure, and the residue was refined by a silica gel column (Wakogel C-300, 20 g, chloroform:methanol=10:0.5), whereby the compound (8) was obtained in an amount of 78.5 mg (82%).

Rf=0.27 (chloroform:methanol=10:0.5).
[α]²⁰ −7.20 (c=0.50, chloroform).
Element analysis $C_{94}H_{112}O_{35}N_2$. Calculated value: C, 61.69; H, 6.17; N, 1.57. Measured value: C, 61.26; H, 6.41; N, 1.73.

EXAMPLE 6

74 mg (0.04 mmol) of the compound (6) was dissolved in 10 ml of methanol, which was catalytically reduced for 15 hours at room temperature by 50 mg of 10% Pd-C. The reaction solution was filtrated by Celite and the solution medium was distilled off under reduced pressure, whereby the compound (8) was obtained in an amount of 51 mg (98%).
Rf=0.54, 0.65 (butanol:ethanol:water=2:1:1).
Element analysis $C_{50}H_{74}O_{34}N_2$. Calculated value: C, 48.15; H, 5.98; N, 2.25. Measured value: C, 48.04; H, 5.88; N, 2.86.

EXAMPLE 7

46 mg (0.037 mmol) of the compound (8) was dissolved in a mixture of 3 ml of pyridine with 3 ml of acetic anhydride. Then, 20 mg of dimethyl aminopyridine was added to the solution, which was stirred for 15 hours at room temperature. The medium of the reaction solution was then distilled off under reduced pressure, and the residue was refined by a silica gel column (Wakogel C-300, 10 g, chloroform:methanol=10:0.5), whereby the compound (9) was obtained in an amount of 55.3 mg (99%).
Rf=0.27 (chloroform:methanol=10:0.5).
Element analysis $C_{62}H_{87}O_{40}N_2$. Calculated value: C, 49.64; H, 5.85; N, 1.87. Measured value: C, 50.00; H, 5.55; N, 2.40.

EXAMPLE 8

48.5 mg (0.032 mmol) of the compound (9) was dissolved in dimethyl formamide, to which 3.6 mg (0.039 mmol) of hydrazinium acetate was added, followed by stirring for 15 minutes at 60° C. After addition of chloroform to the solution, the reaction solution was washed with water and then with saturated brine. The washed solution was then dried by anhydrous magnesium sulfate, followed by distilling-off the solution medium under reduced pressure The residue was then refined by a silica gel column (Wakogel C-300, 10 g, acetone:carbon tetrachloride=2:1), whereby the compound (10) was obtained in an amount of 40 mg (85%).
Rf=0.36 (acetone carbon tetrachloride=2:1).

EXAMPLE 9

33 mg (0.023 mmol) of the compound (10) was dissolved in 1 ml of methylene chloride and, while the solution is cooled by ice, 0.17 ml (1.7 mmol) of trichloroacetonitrile and 6 μl (0.043 mmol) of 1,8-diazabicyclo[5,4,0]-7-undecen were added thereto. The solution was then stirred for 2 hours and the reaction solution was refined by a silica gel column (Wakogel C-300, 10 g, acetone:carbon tetrachloride=2:1), whereby the compound (11) was obtained in an amount of 35 mg (96%).
Rf=0.47 (acetone:carbon tetrachloride=2:1).
NMR 400 MHz, CDCl₃, δ, ppm, TMS 1.874, 1.902, 1.951, 2.025, 2.040, 2.066, 2.088, 2.095, 2.129, 2.133, 2.141, 2.159, 2.164, 2.181, $COCH_3\times15$, 2.553, 2H, m, H-3C, H-3d, 3.800, 3H, s, $OCH_3$, 3.807, 3H, s, $OCH_3$.

EXAMPLE 10

34 mg (0.021 mmol) of the compound (11) and 50 mg (0.066 mmol) of benzoyl ceramide were dissolved in 2 ml of chloroform solution, which was added to 1 g of molecular sieves. Then, after stirring for 10 minutes, 15 μl (0.124 mmol) of boron tetrafluoride-diethylether complex was added to the mixture, while the mixture is cooled by ice-methanol, and the mixture was then stirred for 15 hours. The reaction solution was filtrated by Celite, and then the solution medium was distilled off under reduced pressure. After the distilling-off, the residue was refined by silica gel column (Wakogel C-300, 20 g, ethyl acetate, then chloroform:methanol=10:0.5), and HPTLC (developed at a ratio of acetone:carbon tetrachloride=1:1), whereby 3.6 mg (7.7%) of the compound (12) was obtained.
Rf=0.030 (cholorform:methanol=10:0.5).
[α]_D¹⁹ −7.33 (c=0.15 chloroform).
NMR 400 MHz, CDCl₃, δ, ppm, TMS 0.878, 6H, t, J=6.10, $-CH_3\times2$, 1.252, s, $-CH_2\times32$, 1.869, 1.899, 1.943, 1.964, 2.013, 2.022, 2.025, 2.064, 2.087, 2.125, 2.135, 2.145, 2.158, $-COCH_3\times15$, 2.56, 2H, m, H-3C, H-3d, 3.794, 6H, s, $OCH_3\times2$, 5.454, 1H, dd, J=7.26, 13.22,

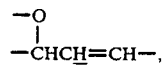

5.859, 1H, d, t, J=13.88, 6.94, $-CH=CH-CH_2-$, 7.443, 2H, t, J=8.06, aromatic proton, 7.548, 1H, t, J=7.57, aromatic proton, 8.006, 2H, d, J=7.08, aromatic proton.

EXAMPLE 11

3.6 mg (0.0016 mmol) of the compound (13) was dissolved in a mixture of 1 ml of methanol with 1 ml of tetrahydrofuran, to which 50 μl of N-sodium methoxide was added. The mixture thus formed was stirred for 15 hours at room temperature. The reaction solution was then neutralized with IRC-50, followed by filtration and distilling-off under reduced pressure. The residue was refined with Sephadex LH-20 (chloroform:methanol:water=60:30:4.6), whereby the compound (13) was obtained in an amount of 2.5 mg (96%). Decomposition point 260° to 275° C.
Rf=0.50 (butanol:ethanol:water=2:1:1).
NMR 400 MHz, d-6 DMSO/D₂O, 98:2 v/v (65°), δ, ppm, TMS 0.854, 6H, t, J=6.72, $CH_3\times2$, 1.241, s, $CH_2\times32$, 1.874, 3H, s, $NHCOCH_3$, 1.882, 3H, s, $NHCOCH_3$, 4.180, 1H, d, J=7.56, H-1a, 4.232, 1H, d, J= 6.59, H-1b, 5.357, H, d, d, J=7.14, 14.5 Hz, $-CH-CH=CH-$, 5.548, 1H, d, t, J=7.14, 14.27, $NHCO-CH=CH-CH_2$ C. Examples concerning the process shown in Process diagram 3

Reference Example 1

2.5 g (4.7 mmol) of the compound (1) was dissolved in 60 ml of EtOH-H₂O-AcOH (20:5:1) and 2.5 g of 10% Pd-C was added to the solution. The mixture was then stirred for 15 hours at 60° C. The reaction solution was filtrated by Celite and the solution medium was condensed under reduced pressure. The residue was dissolved in 200 ml of 80% THF (20% H₂O), to which 2.2 g (8.7 mmol) of iodine was added, followed by stirring at room temperature for 30 minutes. Then, the reaction solution was diluted by water, to which chloroform was added. Then, the mixture was washed with water, further washed by aqueous solution of NaHSO$_3$ and then saturated brine. The washed solution was then dried with MgSO$_4$, and then the solution medium was distilled off. The residual product was then refined by a silica gel column (Wakogel C-300:300 g, chloroform:methanol = 10:0.25), whereby the starting material compound (2) was obtained in an amount of 1.74 g (yield 75%).

Properties of Compound (2)

Rf=0.55 (chloroform:methanol = 10:1).
$[\alpha]_D^{21}$ −30.8 (c=1.02, CHCl$_3$).

Reference Example 2

400 mg (0.81 mmol) of the compound (2) was dissolved in 12 ml of toluene-THF (1:1) mixed solution, and 969 mg (7.57 mmol) of Vilsmeier's reagent was added to the mixture. The mixture was then stirred at 15 hours at room temperature. The reaction liquid was then refined by a silica gel column (Wakogel C-300:20 g, chloroform:methanol = 10:0.5), whereby the compound (3) was obtained in an amount of 300 mg (yield 72.3%).

[Property of Compound (3)]

Rf=0.39 (chloroform:methanol = 10:0.5).

Reference Example 3

10 ml of dichloroethane and 0.2 ml of DMF were added to 450 mg (0.92 mmol) of the compound (2). While cooling the mixture with ice, 200 mg (1.68 mmol) of SOCl$_2$ was added to the mixture, which was then stirred for 15 hours. The medium of the reaction solution was distilled off and then azeotropic process by toluene was conducted, to produce the compound (3) in an amount of 460 mg (yield 98%).

[Properties of Compound (3)]

Rf=0.39 (CHCl$_3$:MeOH=10:0.5).
$[\alpha]_D^{21}$ −63° (c=1.0, CHCl$_3$).
NMR (90 MHz, CDCl$_3$, δ (ppm) TMS): δ 1.917, 2.059, 2.084, 2.089, 2.218, S, OCOCH$_3$×5, 2.80, 1H, dd, J=5.0, 13.0, H-3eq, 3.881, 3H, S, —OCH$_3$, 5.20, 1H, m, H-4.

EXAMPLE 1

2 ml of THF solution of 820 mg (0.92 mmol) of Benzyl O-(2, 3-di-O-benzyl-β-D-guluctopyranosyl)-(1→4)-2,3,6-tri-O-benzyl-β-D-glucopyranoside and 1 ml of THF solution of 150 mg (0.29 mmol) of the compound (3) were added to 1.5 g of molecular sieves. The mixture was stirred at room temperature for 1 hour. While cooled by ice-MeOH, 1 ml of THF solution containing 800 mg (3.1 mmol) of AgOTf and 1 ml of THF solution containing 200 mg (1.05 mmol) of SnCl$_2$ to the mixture. After lapse of 2 hours, 1 ml of THF solution was added to the mixture, which was stirred for 15 hours. The reaction solution was filtrated by Celite and was washed successively by an aqueous solution of saturated bicarbonate, water and saturated brine, followed by drying by anhydrous MgSO$_4$ and distilling-off, whereby a reaction product in an amount of 284 mg (yield 26%) was obtained. The reaction product was then refined by a silica gel column (Wakogel C-300:100 g, toluene:ethylacetate=1:2), whereby the compound (5) and the compound (6) were obtained in amounts of 256 mg (yield 23.5%) and 27 mg (yield 2.5%).

[Property of Compound (5)]

Rf=0.31 (toluene:ethylacetate=1:2).
$[\alpha]_D^{21}$ −53.3 (c=1.01, CHCl$_3$).
Element Analysis. Molecular formula: C$_{74}$H$_{85}$O$_{23}$N + H$_2$O. Calculated value: C, 64.69; H, 6.38; N, 1.02. Measured value: C, 64.66; H, 6.33; N, 1.12.

[Property of Compound (6)]

Rf=0.31 (toluene:ethylacetate=1:2).

Example 2

500 mg (1.02 mmol) of the compound (2) was dissolved in 15 ml of dichloromethane, to which 266 mg (1.2 mmol) of 2,2'-dipyridyldisulfide and 244 mg (1.2 mmol) of tri-n-butylphosphin were added and was then stirred for 5 hours at room temperature. The reaction solution was refined by a silica gel column (Wakogel C-300: 100 g, toluene:ethyl acetate=1:10), thus obtaining 463 mg (yield 76%) of the compound (4).

[Property of Compound (4)]

Rf=0.20 (toluene:ethylacetate=1:10).
$[\alpha]_D^{22}$ +32.5 (c=0.75, CHCl$_3$).
Element Analysis. Molecular formula: C$_{25}$H$_{33}$O$_{13}$NS. Calculated value: C, 49.91; H, 5.53; N, 4.66. Measured value: C, 49.81; H, 5.59; N, 4.55.

EXAMPLE 3

1.5 ml of dichloroethane containing 1 g (1.1 mmol) of Benzyl O-(2, 3-di-O-benzyl-β-D-guluctopyranosyl)-(1→4)-2, 3, 6-tri-O-benzyl-β-D-glucopyranoside and a dichloroethane solution containing 800 mg (3.1 mmol) of AgOTf were added to 1.5 g of molecular sieves. While cooling the mixture by ice-MeOH, 1.5 ml of dichloroethane containing 420 mg (0.7 mmol) of the compound (4) and 200 mg (1.05 mmol) of SnCl$_2$ were added to the mixture, which was stirred at 40° C. for 2 days. The reaction solution was then filtrated by Celite and was then washed by an aqueous solution of saturated sodium bicarbonate and then by saturated brine. The washed solution was then dried with anhydrous MgSO$_4$ and the solution medium was distilled off, whereby 105 mg of the reaction product was obtained. The reaction product was refined by a silica gel column (Wakogel C-300: 100 mg, toluene:ethyl acetate=1:2), thus obtaining 31 mg (yield 3.3%) of the compound (5) and 74 mg (yield 7.8%) of the compound (6).

[Property of Compound (5)]

The same as that in Example 3.

[Property of Compound (6)]

The same as that in Example 3.

EXAMPLE 4

1 ml of pyridine and 1 ml of acetic anhydride were added to 80.3 mg (0.59 mmol) of the compound (6) to dissolve the latter. 20 mg of dimethyl aminopyridine was added to the resultant solution. The solution was then stirred at room temperature for 15 hours and then the medium of the reaction solution was distilled off. The reaction product was then refined by a silica gel column (Wakogel C-300, 15 g, chloroform:methanol=10:0.25), whereby 79 mg (yield 95%) of the compound (7) was obtained.

[Property of Compound (7)]

Rf=0.57 (chloroform:methanol=10:0.25).
$[\alpha]_D^{22}$ −3.0 (c=0.50, CHCl$_3$).
Element Analysis. Molecular formula: $C_{76}H_{88}O_{24}N+2H_2O$. Calculated value: C, 63.58; H, 6.45; N, 0.98. Measured value C, 63.73; H, 6.03; N, 1.12.

EXAMPLE 5

395.7 mg (0.28 mmol) of the compound (5) was dissolved in a mixture of 4 ml of pyridine with 4 ml of acetic anhydride, to which 30 ml of dimethyl aminopyridine was added, followed by stirring for 15 hours at room temperature. The medium of the reaction solution was distilled off and the residual product was refined by a silica gel column (Wakogel C-300, 40 g, chloroform:methanol=10:0.25), whereby 447 mg (yield 109%) of the compound (8) was obtained.

[Property of Compound (8)]

Rf=0.31 (chloroform:methanol=10:0.25).
$[\alpha]_D^{21}$ −4.74 (c=0.95, CHCl$_3$).
Element Analysis. Molecular formula: $C_{76}H_{88}O_{24}N+H_2O$. Calculated value: C, 64.40; H, 6.40; N, 0.99. Measured value: C, 64.26; H, 6.22; N, 1.15.

EXAMPLE 6

440 mg (0.31 mmol) of the compound (8) was dissolved in 40 ml of methanol, and the solution was catalytically reduced for 5 hours at room temperature by 300 mg of 10% Pd-C. The reaction solution was then filtrated and the matrix solution was distilled off, whereby 245 mg (yield 91%) of the compound (9) was obtained.

[Property of Compound (9)]

Rf=0.49 (chloroform:methanol=10:0.5).
Element Analysis. Molecular formula: $C_{34}H_{52}O_{24}N$. Calculated value: C, 47.55; H, 6.10; N, 1.63. Measured value: C, 47.03; H, 5.86; N, 1.88.

EXAMPLE 7

7 ml of pyridine and 7 ml of acetic anhydride were added to 240 mg (0.28 mmol) of the compound (9) so as to dissolve the latter, and 20 mg of dimethyl aminopyridine was added to the solution, followed by stirring at room temperature. The medium of the reaction solution was distilled off, and refining was conducted by a silica gel column (Wakogel C-300: 10 g, chloroform:methanol=10:0.5), thus obtaining 293 mg (yield 94.5%) of the compound (10).

[Property of Compound (10)]

Rf=0.54 (chloroform:methanol=10:0.5).
Element Analysis. Molecular formula: $C_{46}H_{64}O_{30}N$. Calculated value: C, 49.73; H, 5.81; N, 1.26. Measured value: C, 50.13; H, 5.80; N, 1.83.

EXAMPLE 8

150 mg (0.135 mmol) of the compound (10) was dissolved in 1 ml of DMF, to which 14.9 mg (0.162 mmol) of H$_2$N.NH$_2$AcOH was added. The resultant solution was then stirred at 50° C. for 10 minutes. After addition of EtOAc, the reaction solution was washed by water and then by saturated brine, followed by drying by anhydrous MgSO$_4$ and then subsequent distillation. The reaction product was then refined by a silica gel column (Wakogel C-300: 20 g, acetone:fluorine tetrachloride=1:1), whereby 96.9 mg (yield 67.3%) of the compound (11) was obtained.

Property of Compound (11)

Rf=0.32 (acetone:carbon tetrachloride=1:1).
Element Analysis. Molecular formula: $C_{44}H_{62}O_{29}N$. Calculated value: C, 49.43; H, 5.85; N, 1.31. Measured value: C, 49.12; H, 5.83; N, 1.92.

EXAMPLE 9

90 mg (0.084 mmol) of the compound (11) was dissolved in 1 ml of methylene chloride, to which 0.358 ml (3.57 mmol) of trichloroacetonitrile and 12 μl (0.085 mmol) of DBU were added, followed by stirring for 3 hours. The reaction solution was refined by a silica gel column (Wakogel C-300: 15 g, acetone:carbon tetrachloride=1:1), whereby the compound (12) was obtained.

Property of Compound (12)]

Rf=0.47 (acetone carbon tetrachloride=1:1).
NMR (CDCl$_3$ TMS 400 MHz δppm): 1.955, 2.029, 2.046, 2.094, 2.099, 2.122, 2.157, 2.170, 2.181 (—COCH$_3$ group×11), 2.549 (1H, dd, J=4.59, 12.94 Hz, H-3ceq), 3.083 (s, —OCH$_3$), 4.557 (1H, d, J=7.81 Hz, H-1b), 4.836 (1H, m, H-4c), 5.392 (1H, d, J=2.68 Hz, H-4b), 6.504 (d, J=3.91 Hz, H-1a), 8.646 (1H, s, >C=NH).
Decomposition point 250° to 260° C.

EXAMPLE 10

2 ml of chloroform solution containing 98 mg (0.08 mmol) of the compound (12) and 61 mg (0.09 mmol) of the compound (15) was added to 1 g of molecular sieves (sold by Nishio Kogyo Kabushiki Kaisha under commercial name of AW 300). While cooling the mixture by ice-MeOH, 15 μl (0.124 mmol) of BF$_3$.Et$_2$O was added to the mixture. The resultant mixture was then stirred for 15 hours at room temperature and then filtrated by Celite. After distilling-off the mixture medium under reduced pressure, the reaction product was refined by a silica gel column (Wakogel C-300: 20 g, toluene:ethyl acetate=1:2), whereby 51.5 mg (yield 35.3%) of the compound (13) was obtained.

[Property of Compound (13)]

Rf=0.13 (toluene ethyl acetate=1:2).
$[\alpha]_D^{22}$ 10.3 (c=0.75, CHCl$_3$).
NMR (CDCl$_3$ TMS 400 MHz δppm): 0.876 (6H, t, J=5.86, —CH$_3$×2), 1.201 (s, CH$_2$×32), 1.893, 1.945, 2.019, 2.027, 2.029, 2.051, 2.059, 2.127, 2.145, 2.181, 2.359 (COCH$_3$×11), 2.544 (1H, dd, J=4.39), 12.69 (H-1 ceq), 4.519 (1H, d, J=7.08 H-1a), 3.805 (3H, s, OCH$_3$), 4.446 (1H, d, J=8.01, H-1b), 5.860 (1H, m, —CH=CH—CH$_2$—).

EXAMPLE 11

15 mg (0.0083 mmol) of the compound (13) was dissolved in 2 ml of a mixed solvent (MeOH:THF=1:1), to which 30 μl of NaOCH$_3$ was added, followed by stirring for 15 hours at room temperature. After distilling-off the medium of the reaction solution, 1 ml of MeOH, 1 ml of THF and 0.5 ml of H$_2$O was added thereto and stirred for 7 hours at room temperature. The resultant solution was neutralized by IRC-50 and, after filtration, distilling-off was made under reduced pressure. The reaction product was refined by Sephadex LH-20

(CHCl$_3$:MeOH:H$_2$O=60:30:46), whereby 10.3 mg (96.3%) of the compound (14) was obtained.

[Property of Compound (14)]

Rf=0.59 (BuOH:EtOH:H$_2$O=2:1:1).

NMR (d-6DMSO/D$_2$O 98:2 (65° C.) TMS 400 MHz): 0.854 (6H, t, J=6.84, —CH$_3$×2), 1.240 (s, CH$_2$×32), 1.874 (3H, s, NHCOCH$_3$), 1.932 (2H, m, —NH-COCH$_2$—), 2.656 (dd, J=4.88, 11.96, H-3ceq), 3.080 (1H, t, J=8.05, H-2a), 4.174 (1H, d, J=7.81, H-1a), 4.213 (1H, d, J=7.33).

What is claimed is:

1. A process for producing ganglioside GD$_3$ having the general formulae (8) and (9):

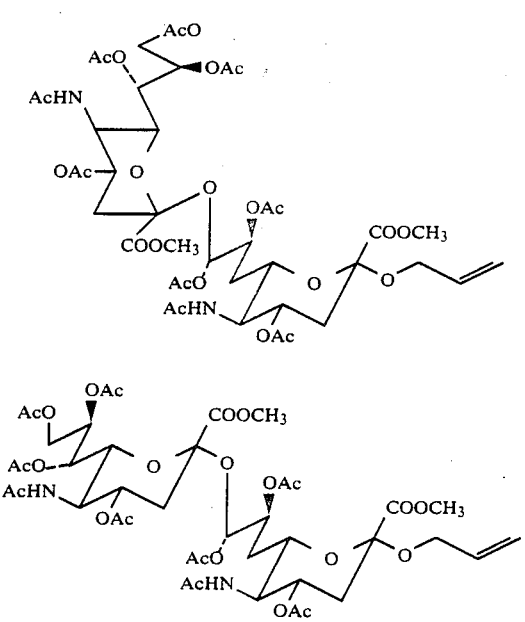

(a) deacetylating a compound (3) having the following formula (3):

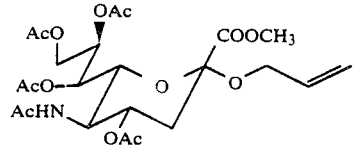

, to produce a compound (4) having the following formula (4):

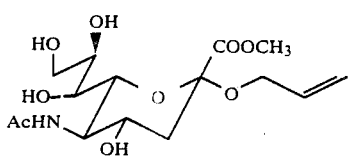

(b) tritylating said compound (4), to produce a compound (5) having the following formula (5):

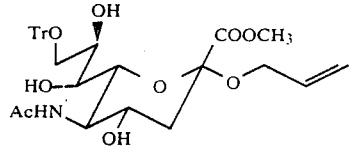

wherein Tr is a trityl group, (c) acetylating said compound (5), to produce a compound (6) having the following formula (6):

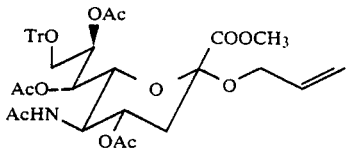

wherein Tr is defined above, (d) detritylating said compound (6), to produce a compound (7) having the following formula (7):

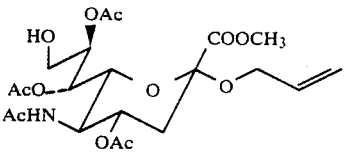

, and then (e) reacting said compound (7) with a compound (2) having the following formula (2):

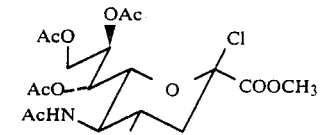

2. A process for producing a compound (7) having the following formula (7):

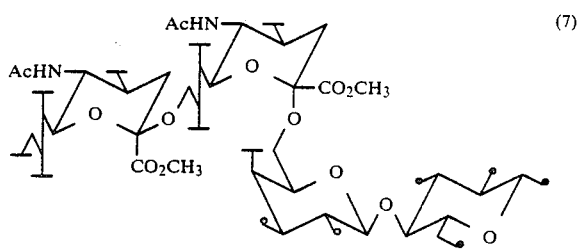

wherein

┝ is an OAc group and

╾ is an OBn group (Bn is a benzyl group), comprising:

(a) deallylating a compound (1) having the following formula (1):

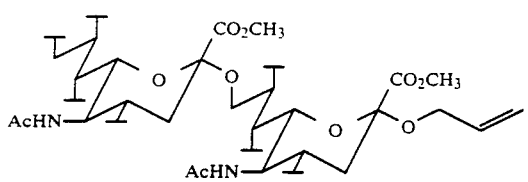
(1)

wherein

⊢ is defined above, to produce a compound (2) having the following formula (2):

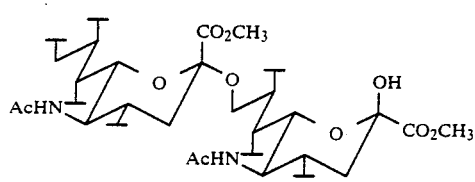
(2)

wherein

⊢ is defined above, (b) chlorinating said compound (2) to produce a compound (3) having the following formula (3):

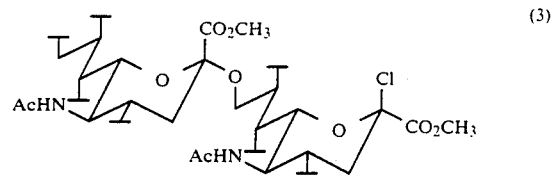
(3)

wherein

⊢ is defined above, (c) reacting said compound (3) with benzyl lactose, to produce compounds (4) and (5) having the following formulae (4) and (5):

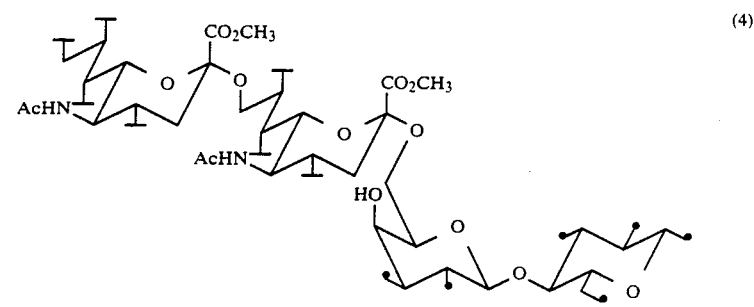
(4)

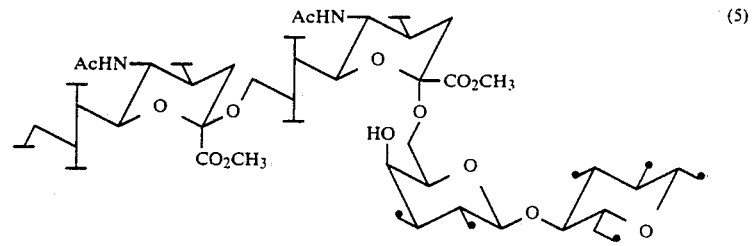
(5)

wherein

⊢ and

⊷ are defined above, and then (d) acetylating said compound (5).

3. A process for producing a compound having the following formula (13):

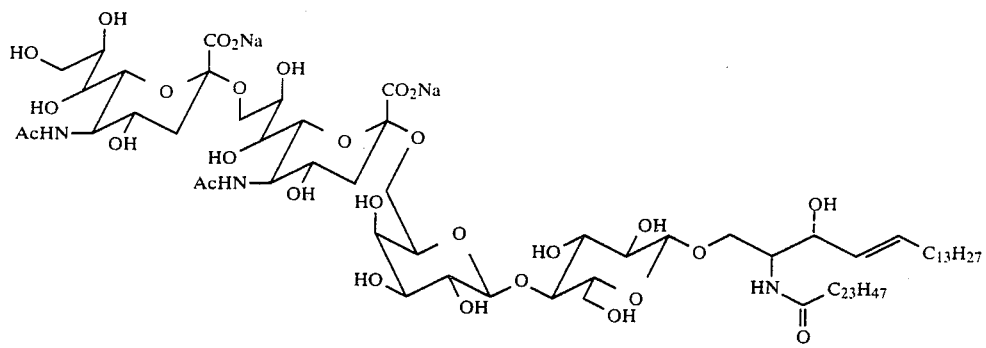
(13)
comprising:
(a) acetylating a compound (4) having the following formula (4):
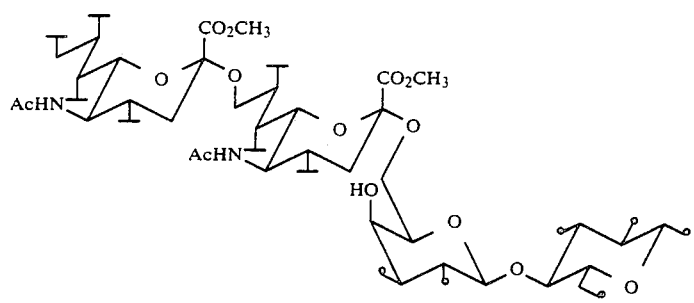
wherein
⊢
is an OAc group and
⊶
is an OBn group (Bn is a benzyl group), to produce a compound (6) having the following formula (6):
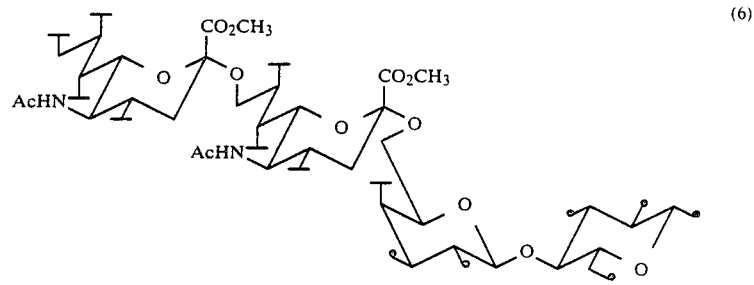
(6)
wherein
⊢
and
⊶
are defined above, and then
(b) debenzylating said compound (6), to produce a compound (8) having the following formula (8):

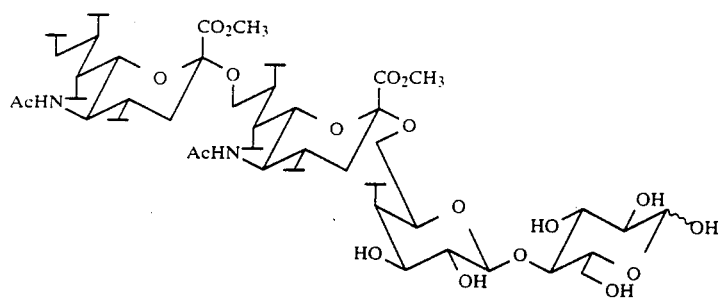
(8)

wherein ⊢ is defined above, (d) selectively deacetylating said compound (9), to produce a compound (10) having the following formula (10):

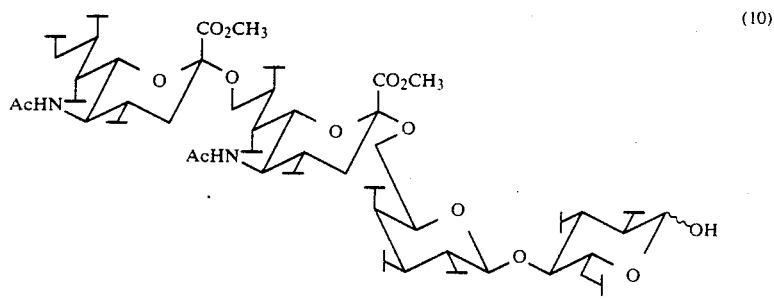
(10)

wherein ⊢ is defined above.

(c) acetylating said compound (8), to produce a compound (9) having the following formula (9):

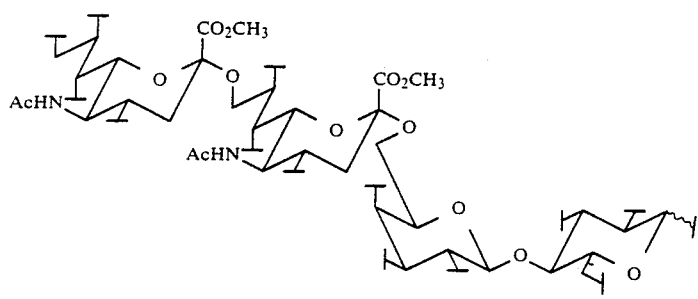
(9)

wherein ⊢ is defined above, (e) reacting said compound (10) with trichloroacetonitrile to produce a compound (11) having the following formula (11):

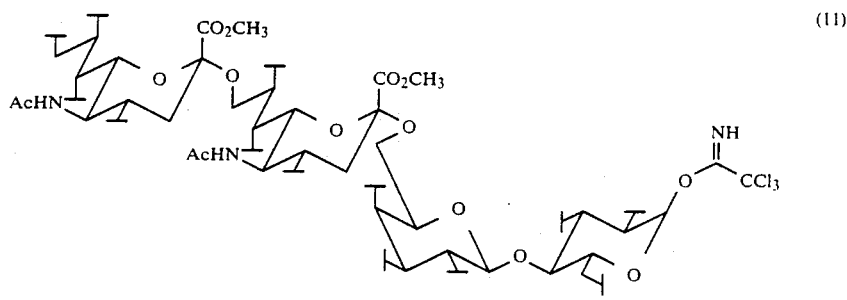
(11)

wherein

├─ is defined above, (f) reacting said compound (11) with benzoylceramide, to produce a compound (12) having the following formula (12):

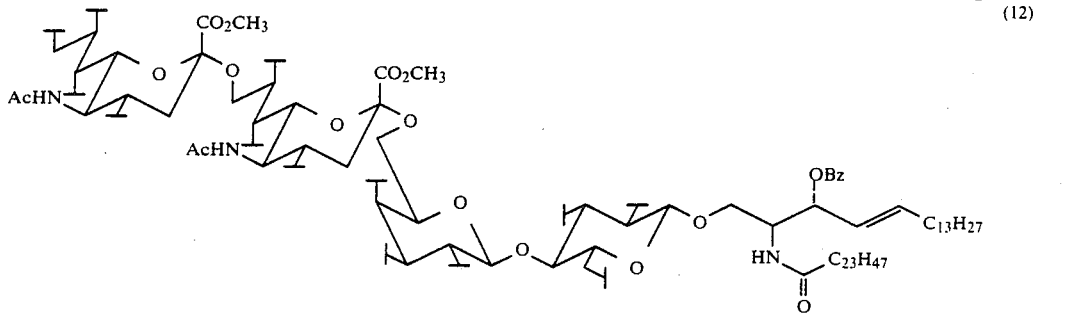

wherein

├─ is defined above and Bz is a benzoyl group, and then (g) hydrolyzing said compound (12).

4. A process for producing a compound (7) having the following formula (7):

(7)

wherein

├─ is an OAc group and

○─ is an OBn group (Bn is a benzyl group), comprising acetylating a compound (6) having the following formula (6):

(6)

wherein

├─ and

○─ are defined above.

5. The process of claim 4, wherein said compound (6) is one of the compounds obtained by reacting benzyl lactose with a compound (3) or (4) having the following formula (3) or (4).

(3)

or (4)

wherein

├─ is an OAc group.

6. The process of claim 5, wherein said compound (4) is obtained by pyridylsulfidizing a compound (2) having the following formula (2):

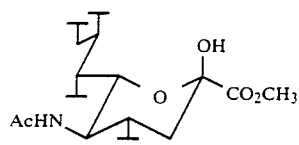
(2)

wherein

⊢ is an OAc group.

7. A process for producing a compound (14) having the following formula (14):

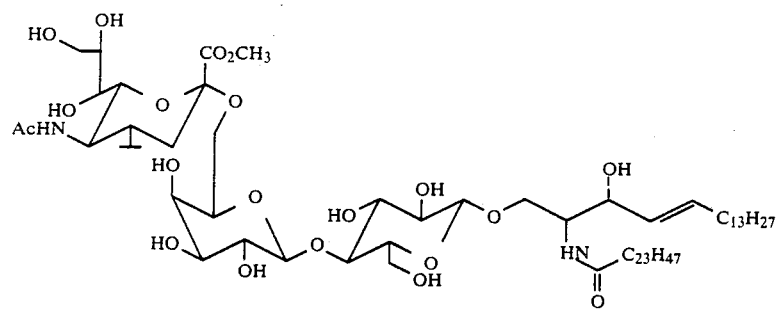
(14)

comprising:
(a) acetylating a compound (5) having the following formula (5):

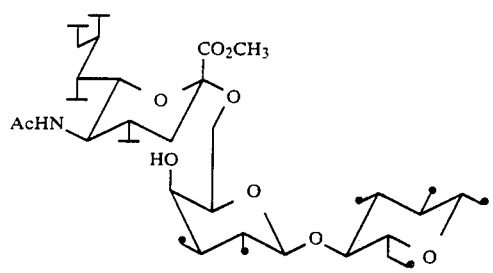
(5)

wherein

⊢ is an OAc group and

⌐ is an OBn group (Bn is a benzyl group), to produce a compound (8) having the following formula (8):

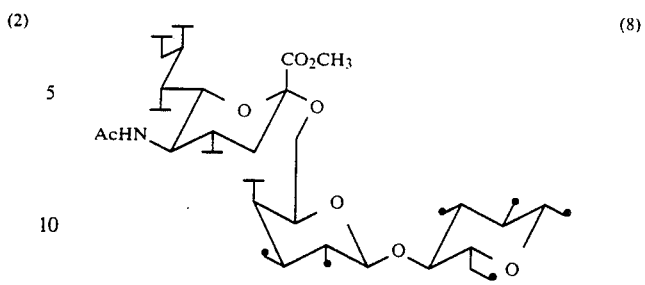
(8)

wherein

⊢ and

⌐ are defined above,
(b) debenzylating said compound (8), to produce a compound (9) having the following formula (9):

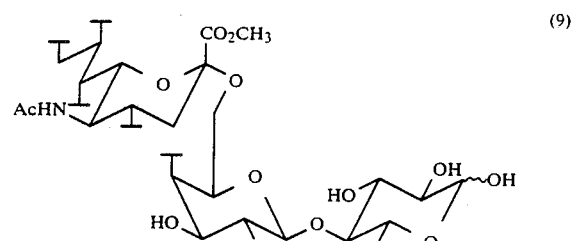
(9)

wherein

⊢ is defined above,
(c) acetylating said compound (9), to produce a compound (10) having the following formula (10):

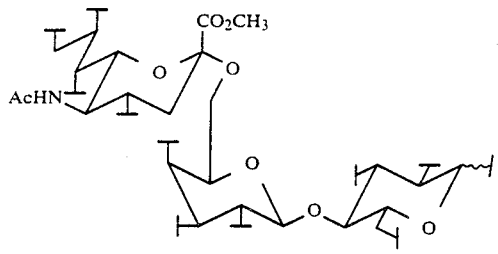
(10)

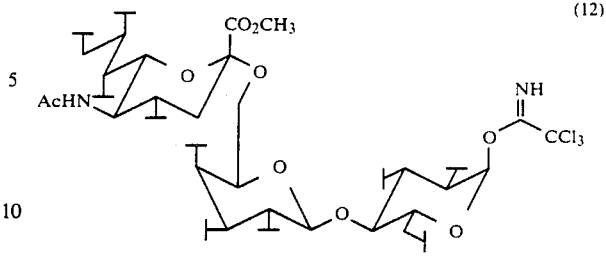
(12)

wherein

⊢ is defined above,
(d) deacetylating said compound (10), to produce a compound (11) having the following formula (11):

wherein

⊢ is defined above,
(f) reacting said compound (12) with benzoylceramide, to produce a compound (13) having the following formula (13):

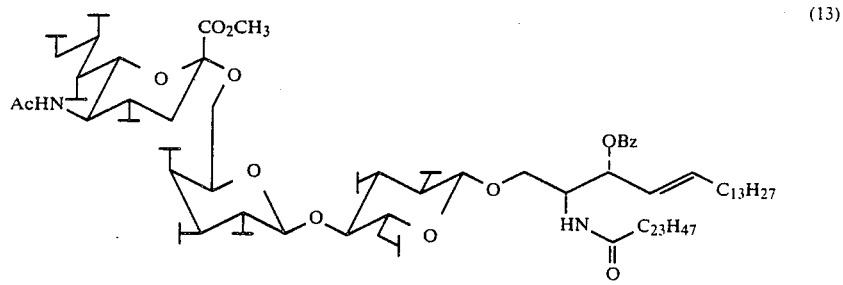
(13)

wherein

⊢ is defined above, and then
(g) deactylating, debenzylating and then saponifying said compound (13).

8. The process of claim 7, wherein said compound (5) is one of the compounds obtained by reacting benzyl lactose with a compound (3) or (4) having the following formula (3) or (4):

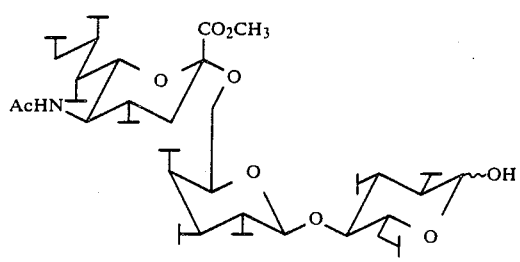
(11)

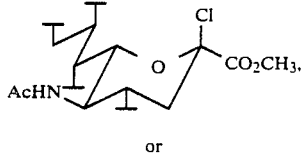
(3)

or

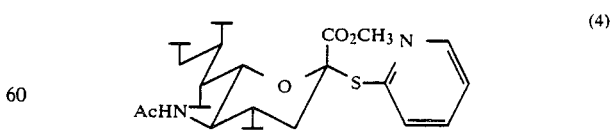
(4)

wherein

⊢ is defined above,
(e) reacting said compound (11) with Cl₃CCN, to produce a compound (12) having the following formula (12):

wherein

⊢ is an OAc group.

9. The process of claim 8, wherein said compound (4) is obtained by pyridylsulfidizing a compound (2) having the following formula (2):

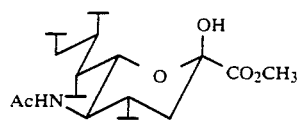
(2)

wherein

is an OAc group.

10. A sialic acid derivative having the formula (I):

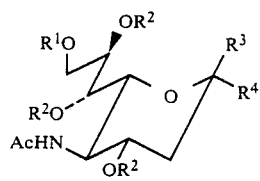

wherein $R^1$ represents

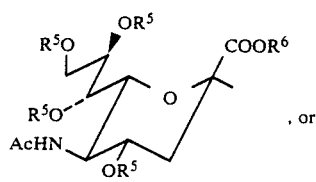

, or

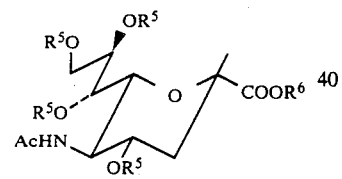

($R^5$ represents hydrogen or an acetyl group and $R^6$ represents hydrogen, sodium or a methyl group)
$R^2$ represents hydrogen or an acetyl group,
one of $R^3$ and $R^4$ represents —OCH$_2$CHCH$_2$, or

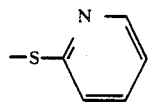

while the other represents —COOR$^{11}$, wherein $R^{11}$ represents hydrogen, sodium or a methyl group.

11. A sialic acid derivative having the formula (I):

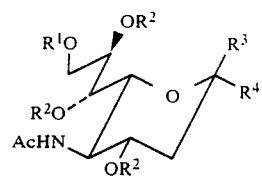

wherein $R^1$ represents hydrogen, an acetyl group, a trityl group,

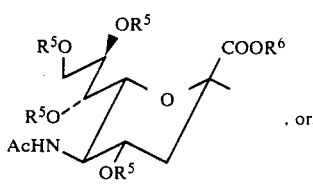

, or

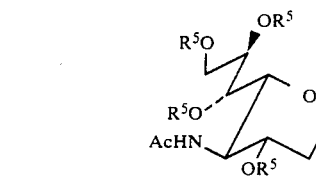

($R^5$ represents hydrogen or an acetyl group and $R^6$ represents hydrogen, sodium or a methyl group)
$R^2$ represents hydrogen or an acetyl group,
one of $R^3$ and $R^4$ represents

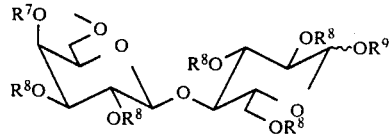

($R^7$ represents hydrogen or an acetyl group, $R^8$ represents hydrogen, an acetyl group or a benzyl group, $R^9$ represents hydrogen, an acetyl group, a benzyl group or

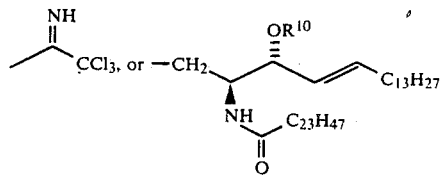

wherein $R^{10}$ represents hydrogen or a benzoyl group), while the other represents —COOR$^{11}$ wherein $R^{11}$ represents hydrogen, sodium, or a methyl group.

* * * * *